United States Patent [19]
Granger et al.

[11] 3,939,069
[45] Feb. 17, 1976

[54] ARTIFICIAL KIDNEY AND A METHOD OF ULTRAFILTERING A LIQUID

[75] Inventors: Alain Granger, Lesigny; Andre Sausse, Sceaux, both of France

[73] Assignee: Rhone-Poulenc-Textile, Paris, France

[22] Filed: Dec. 6, 1972

[21] Appl. No.: 312,515

[30] Foreign Application Priority Data
Dec. 6, 1971 France .............................. 71.43720

[52] U.S. Cl. ............... 210/22 A; 210/90; 210/321 B
[51] Int. Cl.² .................... B01D 31/00; B01D 13/00
[58] Field of Search ............... 210/22, 90, 321, 195

[56] References Cited
UNITED STATES PATENTS

| | | | |
|---|---|---|---|
| 3,506,126 | 4/1970 | Serfass et al. .................... | 210/195 X |
| 3,527,700 | 9/1970 | Goldhaber ...................... | 210/321 X |
| 3,669,880 | 6/1972 | Marantz et al. ..................... | 210/22 |
| 3,697,418 | 10/1972 | Johnson ............................ | 210/321 X |
| 3,783,127 | 1/1974 | Cook et al. ..................... | 210/321 X |

OTHER PUBLICATIONS

Kiil et al., "Parallelflow Plastic Hemidialyser as a Membrane Oxygenator", from Trans. Amer. Soc. for Artif. Organs, Vol. VIII, 1962 (pp. 43–46).

*Primary Examiner*—Frank A. Spear, Jr.
*Attorney, Agent, or Firm*—Cushman, Darby & Cushman

[57] ABSTRACT

A method of ultrafiltration and an artificial kidney therefor, in which a membrane which is capable of simultaneous ultrafiltration and dialysis of blood is arranged to form a portion of the wall of a constant volume, closed loop vessel. A dialysis liquid is circulated in the vessel, while blood is passed on the opposite face of the membrane, and a fraction of the dialysis liquid is withdrawn from the vessel at a predetermined rate. The remainder of the dialysis liquid is kept at a constant temperature and is regenerated.

12 Claims, 1 Drawing Figure

U.S. Patent  Feb. 17, 1976  3,939,069
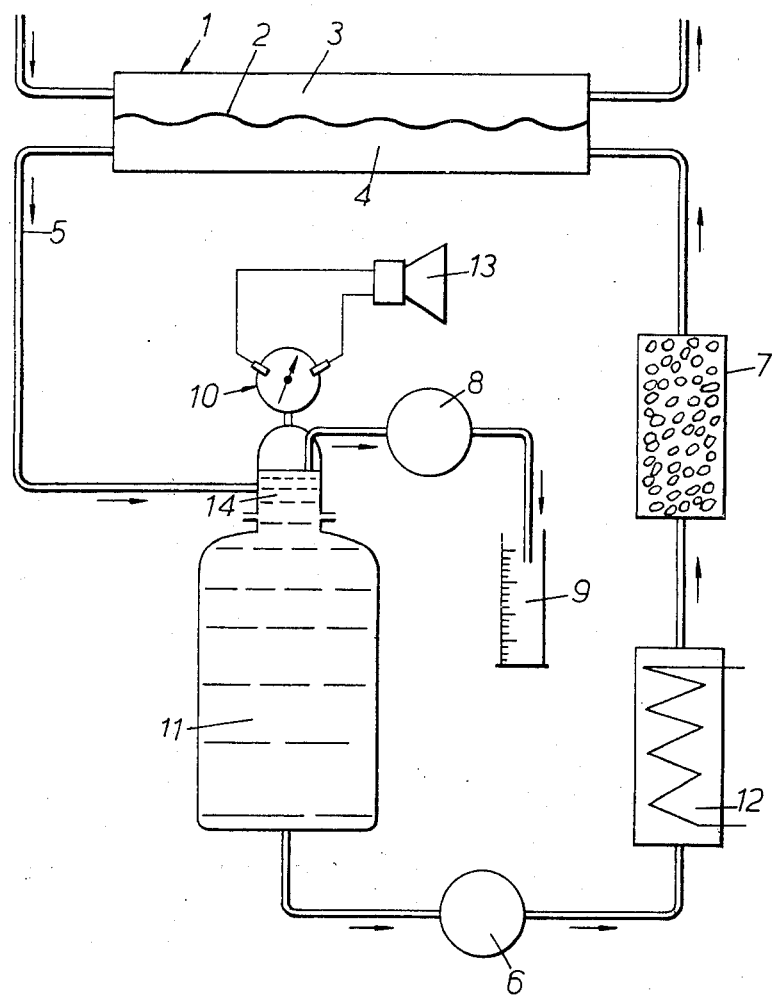

ARTIFICIAL KIDNEY AND A METHOD OF ULTRAFILTERING A LIQUID

The present invention relates to a method of ultrafiltration, for example for carrying out haemodialysis treatments, and to artificial kidneys.

Patients who are partly or totally deprived of the kidney functions are conventionally subjected to periodic sessions of haemodialysis. During each session it is necessary to withdraw by ultrafiltration through the dialysis membrane exact quantities of water so as to prevent hypertension or even the formation of oedema. The general condition of the patient in fact depends on the quantity of water which has been removed.

Thus at present water is withdrawn during the course of a haemodialysis session by regulating the value of the reduced pressure of the dialysis liquid but since the ultrafiltrate is evacuated together with the dialysis liquid the amount of water actually extracted during the course of the dialysis is generally unknown.

In fact, this amount depends on a number of other factors: for example on the composition of the blood which varies during the haemodialysis, on the precision with which the pressures of the blood and of the dialysis liquid at the level of the membranes are known, on the nature of the membrane and on the extent of its clogging, and the greater the rate of ultrafiltration permitted by the membrane the more irregular does the amount of actually withdrawn water become. In this way haemodialysis techniques at present lead paradoxically to results which are more haphazard the better the quality of ultrafiltration provided by the membrane.

It is, of course, possible to make corrections a posteriori, but these must not be made too quickly so as not to unbalance the cellular medium. Hence, it is desirable to be able to draw up an ultrafiltration programme before the haemodialysis session rather than to have to make corrections thereafter.

On the other hand, present-day membranes may lead to excessively high ultrafiltrate flow, particularly in the treatment of children. It is then necessary to reduce this flow to acceptable values and in some cases even to stop all ultrafiltration.

According to the present invention we provide a method of ultrafiltration of a liquid comprising providing a constant volume closed vessel having a wall portion forming a membrane of an ultrafiltration apparatus, connecting the face of said membrane remote from said constant volume closed vessel to the liquid to be ultrafiltered, filling said vessel with dialysis liquid and withdrawing a fraction of said dialysis liquid from the vessel at a predetermined rate. With such a method one can use a simple and safe means of ensuring predetermined ultrafiltration flow during a haemodialysis session so as to progressively and with precision restore the patient to his normal weight at the end of each session.

The invention further permits optimum utilisation of the capacities of dialysis membranes giving high rates of ultrafiltration.

According to the method of the invention, the withdrawn liquid is simultaneously replaced by an equal volume of blood ultrafiltrate through the membrane.

The expression "dialysis liquid" will for purposes of simplification hereafter denote the liquid contained in the vessel, it being understood that this liquid may contain increasing amounts of ultrafiltrate during the course of a treatment. The proportion of ultrafiltrate generally remains small and represents at most a few percent of the volume.

It is not necessary totally to eliminate the gas (such as air) from the vessel as long as the volume of residual gas does not prolong the response time of the apparatus beyond acceptable limits. A gaseous residue of a volume less than 500 cm$^3$, and preferably less than 200 cm$^3$, can be tolerated.

The pressure difference at either side of the haemodialysis membrane is not critical, it depends particularly on the nature of the membrane (permeability, mechanical resistance), on the flow of ultrafiltration, on the degree of clogging and on the difference of osmotic pressure between the blood and the dialysis liquid. All the same it is advantageous to hold this pressure difference within predetermined limits, exceeding of these limits being an indication of a malfunction. Since the blood pressure is almost constant it is generally satisfactory to monitor the pressure of the dialysis liquid prevailing in the vessel. This pressure is generally lower than atmospheric pressure (up to 500 mm. of mercury, raised in the event of clogged membranes), but it may be slightly higher than atmospheric (very permeable membranes, ultrafiltration regulated at very weak values). When haemodialysis is performed without ultrafiltration the pressure in the vessel simply compensates for the osmotic pressure of the blood with respect to the dialysis bath, i.e. about 30 mm. of mercury.

The dialysis liquid can be withdrawn from the vessel by any convenient apparatus, for example a pump (whether volumetric or not) or vacuum generator. During the course of the withdrawal, gas is extracted which is either initially dissolved in the dialysis liquid or in the ultrafiltrate, or which has diffused through the membrane. The volume of withdrawn liquid may be measured after degassing, for example in a graduated test tube. If desired, the operation of the withdrawal device may be controlled by a programming means provided with a detector which is susceptible to the volume or to the flow of degassed liquid has been withdrawn.

According to another apsect of the invention there is provided an artificial kidney comprising a haemodialyser, including a membrane capable of permitting simultaneous dialysis and ultrafiltration of blood, a chamber on one face of the membrane connectable to a blood stream, a constant volume closed vessel, having a wall portion formed by said membrane, said vessel containing a dialysis liquid and means for withdrawing from said constant volume closed vessel, at a predetermined rate, a fraction of the dialysis liquid. Various other devices may be added: thermostat, dialysis liquid regenerator (for example a cartridge of adsorbent charcoal, of urease/ammonia absorber complex (resin or zirconium phosphate), source of hypochloride), manometer with high and low pressure contacts and other safety devices for example shut-off taps.

The connecting tubes are preferably thick-walled tubes of the "vacuum tube" kind.

The dialysis liquid reservoir is designed to withstand without noticeable deformation the reduced pressure to which it may be exposed, i.e. having thick or ribbed walls. Materials such as glass, stainless steel and polymers which can stand sterilising are suitable for its manufacture.

In a normal dialysis about 300 liters of dialysis liquid are generally consumed, which necessitates a voluminous apparatus.

It is preferred to utilise the compact apparatuses which have recently been developed and wherein various regeneration systems make it possible to operate with a reduced volume of liquid which circulates in closed circuit, the waste matter (urea, uracic acid, creatinin for example) being fixed or destroyed by systems such as those indicated above.

It is possible further to reduce the volume of the dialysis liquid if one accepts the blood being allowed to be charged with urea beyond the usual values. It is known that human beings can stand up to about 4 g/l of urea and it is, therefore, possible not to perform a haemodialysis unless the blood is charged with as much as 3 g/l of urea, for example. A volume of dialysis liquid in the region of 40 liters (i.e. the water volume of an average patient) thus theoretically enables the urea content to be reduced by 50 percent, i.e. to bring it back to 1.5 g/l without regeneration. The quantity of urea thus extracted corresponds substantially to that which is formed in 3 days.

Although such a volume of 40 liters is sufficient for conveniently extracting the other waste matter from the blood, it is useful to add a regenerator of the aforesaid kind to the circuit in order to increase the speed and efficacy of the haemodialysis.

In order that the invention will be better understood, the following description is given, merely by way of example, reference being made to the accompanying drawing, in which the sole FIGURE schematically illustrates to no particular scale, one embodiment of an artificial kidney according to the invention.

A haemodialyser 1 is provided with a dialysis membrane 2 permitting ultrafiltration of the blood. This membrane separates the compartment 3 intended for circulation of the blood to be purified from the compartment 4 intended for the dialysis liquid. The dialysis liquid is contained in a vessel 5 forming a closed circuit of constant volume and comprising the compartment 4, a reservoir 11, a circulation pump 6, which recycles the dialysis liquid within the circuit 5 according to a flow rate corresponding to the normal conditions of a haemodialysis operation, a temperature regulating vessel 12 and a cartridge 7.

The reservoir 11 which has a volume of 40 liters may be formed of stainless steel. It is advantageously provided, at its upper portion, with a transparent glass inspection window 14. An extraction pump 8 of the volumetric type sucks dialysis liquid from the vessel 5 through a short dip tube and expels it into a graduated receptacle 9. A manometer 10 indicates at any instant the reduced pressure prevailing at a specific point of the zone 5. It is equipped with minimum and maximum contacts connected to an alarm device 13, for example an acoustic device. The cartridge 7 filled with activated charcoal is positioned in the return path to the haemodialyser. The temperature regulating means in the vessel 12 maintains the dialysis liquid at a value of 37° to 38°C.

The apparatus operates as follows. A suitable volume of dialysis liquid, prepared and controlled according to conventional techniques (for example conductivity measurements) is introduced into the vessel 5: the inspection window 14 enables the level of the liquid to be watched, which level should be as close as possible to the end of the dip tube. By means of the device 12 the temperature of the dialysis liquid is brought to and maintained at the desired temperature.

In a parallel operation the compartment 3 of the haemodialyser is filled with physiological serum, its inlet is connected to an artery of the patient, the serum is displaced by the blood and the outlet of the compartment is connected to a vein of the patient.

The circulation of the dialysis circuit having been effected by the pump 6 the dialysis can then begin. The dialysis liquid passes through the cartridge of activated charcoal 7 which fixes part of the impurities. Under the effect of the reduced pressure created by the pump 8 the ultrafiltration in turn begins. The gases dissolved in the blood pass through the membrane 2 and accumulate at the top of the reservoir 11.

The pump 8, which may for example be a peristaltic pump, first sucks the dialysis liquid or the surplus air at the top of the reservoir 11. The dialysis liquid is thus brought to a constant level corresponding to the end of the dip tube disposed at the suction side of the pump. The dialysis liquid withdrawn from the reservoir is collected in the calibrated receptacle 9, the speed of the pump 8 being regulated so as to obtain a flow of degassed dialysis liquid equal to the desired flow of ultrafiltrate. The manometer 10 simply indicates the reduced pressure prevailing in the circuit 5. If, for any reason, the value of this reduced pressure strays from the previously fixed limits, then the alarm signal is triggered.

The method according to the invention offers considerable advantages. The ultrafiltration flow is in fact enforced, i.e. fixed beforehand at the desired values, and it can, moreover, be controlled and if need be readily corrected at any time during the dialysis. This flow is thus rendered independent of any of the factors on which it had hitherto been dependent when the dialysis liquid was subjected to a reduced pressure of a set value. Mastery of the ultrafiltration is a decisive element in the sphere of haemodialysis.

Furthermore, this method is very reliable. In fact, the alarm system linked to the manometer placed on the vessel containing the dialysis liquid signals as soon as any incident occurs. Thus the "low pressure" alarm can signal an excessive withdrawal flow and thus protects the membrane; the "high pressure" alarm can signal rupture of the membrane or of a tubing or, on the other hand, choking of tubing (by crushing). Moreover, if an incident occurs in the blood circuit (tube chocked or broken, pressure drop in the patient) it causes in the haemodialyser a sudden variation of blood pressure, the ultrafiltering liquid transmits it in full to the dialysis liquid and triggers the alarm.

Finally, the apparatus used can be appreciably simpler than conventional apparatus. More particularly, the auxiliary apparatus conventionally used as generator of the dialysis bath and monitor of the haemodialysis is no longer required. In fact, the complete dose of dialysis liquid can be prepared beforehand and the composition of the dialysis liquid can be controlled prior to the haemodialysis session and, if desired, adjusted to the ideal value; thus the conductivity meter becomes unnecessary during the haemodialysis session. Moreover, since escape of blood is automatically restricted to the flow of dialysis liquid withdrawn and since, furthermore, the inspection window 14 enables the level and colouration of the dialysis liquid to be verified at any time, the colorimeter can be replaced by a visual control means. In fact, the control apparatus for the haemodialysis is in essence reduced to the manometer 10 with its alarms and for the ultrafiltration to the calibrated receptacle 9.

The method according to the invention is of special interest for haemodialysis. It can readily be adapted to the case of pure ultrafiltration. It suffices to connect the pump 8 to a non-deformable compartment adjacent to the downstream face of the membrane of a blood ultrafilter, having possibly filled the compartment with a liquid (ultrafiltrate or liquid of some other kind), and to extract a quantity of liquid equal to the desired volume of ultrafiltrate.

The Examples which follow illustrate the invention and show the usefulness of the method for evaluating membranes having good ultrafiltration characteristics.

EXAMPLE 1

The apparatus schematically represented in the FIGURE is employed. The haemodialyser 1 is of the kind described in French Pat. No. 1,597,874. It is equipped with a haemodialysis membrane of regenerated cellulose commercially obtainable under the name of "Cuprophan" having a surface of 0.9 m², which permits an ultrafiltration flow of 1.7 milliliters per hour, per m² and per mm. of mercury. The reservoir 11 is a stainless steel vessel of 40 liters volume provided with an inspection window 14 at the upper portion. The manometer 10 comprises two alarms for high and low pressure.

The circulation pump 6 is of the centrifugal kind.

The extraction pump 8 is a volumetric, of peristaltic type, having a thick-walled tube. The receptacle 9 is a calibrated test tube of 5 liters. A cartridge 7 of polypropylene contains 500 g. of activated charcoal. The device 12 consists of an electric resistance of 1 kW and a regulation device enabling the temperature of the dialysis liquid to be maintained at 38°C. These various members are connected by tubes of silicon elastomer having thick walls (diameters 8–14 mm).

The constant volume vessel or circuit 5 is filled with dialysis liquid from the highest connection, according to conventional technique. At the top of the reservoir 11 a volume of air of 100 cm³ remains. The dialysis liquid is caused to circulate and its conductivity is checked. The haemodialyser is connected to a ewe of 55 kg. and the treatment is begun.

The speed of the pump 8 is regulated as a function of a flow of degassed ultrafiltrate of 200 cm³/h and an hourly check is made that the drawn off flow in fact corresponds to that desired (the speed of the pump 8 is altered if necessary).

The session lasted 10 hours during which time the blood pressure in the dialyser was held steady near +60 mm. of mercury and the pressure at the manometer 10 near −100 mm. of mercury gauge. The urea rate of the ewe's blood changed from 2.5 g/l to 1.35 g/l. The rates of creatinin and of uracic acid in the dialysis liquid were almost zero after passing through the activated charcoal. Furthermore, 2 liters of liquid were withdrawn from the ewe by ultrafiltration.

EXAMPLE 2

The same apparatus as in Example 1 was employed but the Cuprophan membrane was replaced by a membrane of a copolymer of acrylonitrile and sodium methallylsulphonate, 89.5% acrylonitrile, having undergone an aqueous thermal treatment at 90°C. with a stretching of 180 percent. This membrane permits an ultrafiltration flow six times as large as the preceding membrane, all other conditions being the same.

A test similar in every respect to that described in Example 1 was carried out, in particular the extraction pump 8 was driven at the same speed so as to obtain extraction of an equal volume of ultrafiltrate. The pressure at the manometer 10 was held steady in the neighbourhood of +10 mm. of mercury.

EXAMPLE 3

The same apparatus as in Example 2 is used but without operating the pump 8 other than to evacuate the small volume of gas released during the dialysis.

After 10 hours of treatment the purification of the blood was as satisfactory as in Example 2 but the ewe had not lost any weight.

During the operation the manometer 10 has indicated a pressure in the neighbourhood of +30 mm. Hg.

We claim:

1. A method of ultrafiltration of a liquid comprising the steps of providing a constant volume closed system having a wall portion forming a membrane of an ultrafiltration apparatus, connecting the face of the membrane remote from said constant volume closed system to the liquid to be ultrafiltered, filling said system with a dialysis liquid, circulating the dialysis liquid along said membrane at a flow rate corresponding to the normal conditions of a haemodialysis operation and withdrawing by pumping a fraction of said dialysis liquid from the system at a predetermined rate, so that the volume of liquid in said system is maintained constant.

2. A method as claimed in claim 1, and further comprising maintaining the pressure of the dialysis liquid between two predetermined values lower than the pressure of the liquid to be ultrafiltered at said membrane.

3. A method as claimed in claim 1, wherein the dialysis liquid is recycled and purified within said constant volume closed vessel.

4. A method as claimed in claim 3, wherein the impurities contained in the diaylsis liquid are fixed with the aid of activated charcoal.

5. A method as claimed in claim 1, and further comprising the steps of withdrawing residual gases from said constant volume vessel with said fraction of the dialysis liquid, degassing said dialysis liquid and measuring the rate of withdrawal of the degassed dialysis liquid.

6. A method as claimed in claim 5, and further comprising the steps of controlling the withdrawal rate of dialysis liquid from said constant volume vessel as a function of the rate of withdrawal of the degassed dialysis liquid.

7. Method of claim 1, wherein the dialysis liquid is circulated in the constant volume closed system without substantial valve restriction of the dialysis liquid flow.

8. An artificial kidney comprising, in combination:
   a. a haemodialyser including a membrane capable of permitting simultaneous dialysis and ultrafiltration of blood;
   b. a chamber on one face of said membrane connectable to a blood stream;
   c. a constant volume closed system, having a wall portion formed by said membrane, said system containing a dialysis liquid;
   d. means for circulating the dialysis liquid along said membrane at a flow rate corresponding to the normal conditions of a haemodialysis operation; and
   e. means for withdrawing by pumping from said constant volume closed system, at a predetermined rate, a fraction of the dialysis liquid, so that the volume of liquid in the system is maintained constant.

9. An artificial kidney as claimed in claim 8, wherein said constant volume closed vessel comprises a closed circuit loop including said haemodialyser, a reservoir, a circulating pump and heating and temperature regulating means, and wherein said means for withdrawing dialysis liquid includes means for pumping dialysis liquid from said reservoir and means for measuring the rate of withdrawal of degassed dialysis liquid.

10. An artificial kidney as claimed in claim 9, and further comprising, in said closed circuit loop, a dialysis liquid generator.

11. An artificial kidney as claimed in claim 9, and further comprising a manometer associated with said reservoir and alarm means operatively associated with the manometer effective to give a warning when the pressure within said reservoir deviates from the predetermined range.

12. An artificial kidney as claimed in claim 8, wherein said means for circulating the dialysis liquid circulates the dialysis liquid without substantial valve restriction of the dialysis liquid flow.

* * * * *

UNITED STATES PATENT OFFICE
CERTIFICATE OF CORRECTION

Patent No. 3,939,069      Dated February 17, 1976

Inventor(s)     Alain Granger and Andre Sausse

It is certified that error appears in the above-identified patent and that said Letters Patent are hereby corrected as shown below:

In the heading at [73] change the name of the assignee to --Rhone-Poulenc S.A.--

Signed and Sealed this

Tenth Day of August 1976

[SEAL]

*Attest:*

RUTH C. MASON
*Attesting Officer*

C. MARSHALL DANN
*Commissioner of Patents and Trademarks*